US00PP25916P3

(12) United States Plant Patent
Ranney

(10) Patent No.: US PP25,916 P3
(45) Date of Patent: Sep. 22, 2015

(54) ***DEUTZIA* PLANT NAMED 'NCDX1'**

(50) Latin Name: ***Deutzia* sp.**
Varietal Denomination: NCDX1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 182 days.

(21) Appl. No.: 13/987,430

(22) Filed: Jul. 24, 2013

(65) Prior Publication Data

US 2015/0033425 P1 Jan. 29, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV—PLUTO: Plant Variety Database, International Union for the Protection of New Varieties of Plants; Mar. 12, 2015, citation for 'NCDX1'.*
Flowering Shrubs, Spring Meadow Nursery, Inc. Starter Plants Catalog and Shrub Reference 2012-2013; Sep. 12, 2012, pp. 1, 2, 11 and 34 (4 pgs total).*
Flowering Shrubs, Spring Meadow Nursery, Inc. Starter Plants Catalog and Shrub Reference 2012-2013; Sep. 12, 2012, pp. 1, 2, 11 and 34.
United States Postal Service Bulk Mailing Sheet for 2012/2013 Spring Meadows Nursery Catalogue (Sep. 7, 2012).
Plant Breeders' Right Application filed in Canada on Sep. 12, 2012.

* cited by examiner

*Primary Examiner* — Susan McCormick Ewoldt
(74) *Attorney, Agent, or Firm* — Myers Bigel Sibley & Sajovec, PA

(57) ABSTRACT

NCDX1' is a new *Deutzia* plant distinguished by a compact, low-growing, rounded/spreading plant habit and prolific, white flowers.

2 Drawing Sheets

Latin name of the genus and species: The Latin name of the novel plant variety disclosed herein is *Deutzia* sp.

Variety denomination: The inventive variety of *Deutzia* sp. disclosed herein has been given the varietal denomination 'NCDX1'.

BACKGROUND OF THE INVENTION

The present invention comprises a new and distinct cultivar of *Deutzia,* botanically known as *Deutzia* sp., and hereinafter referred to by the name 'NCDX1'. This new *Deutzia* is a product of a breeding program conducted by the inventor in Mills River, N.C. The objective of the breeding program was to develop new *Deutzia* cultivars with improved flowering characteristics and smaller growth habits.

The new *Deutzia* plant originated from controlled crosses in Mills River, N.C. in March 2007 between *Deutzia gracilis* 'Nikko', not patented, as the female parent and *Deutzia*× *rosea* 'Carminea', not patented, as the male parent.

The first asexual reproduction of *Deutzia* sp. 'NCDX1' was carried out in May, 2007 by rooting stem cuttings in Mills River, N.C. *Deutzia* sp. 'NCDX1' roots readily from softwood cuttings treated with a basal dip of 2,000 to 4,000 ppm indole butyric acid (potassium salt) in water. 'NCDX1' has been found to retain its distinctive characteristics through successive asexual propagations of stem cuttings.

SUMMARY OF THE INVENTION

The following are the unique and distinguishing characteristics of *Deutzia* sp. 'NCDX1' when grown under normal horticultural practices in Mills River, N.C. These characteristics been repeatedly observed and in combination distinguish 'NCDX1' as a new and distinct cultivar:

1. Compact, low-growing, rounded/spreading plant habit.
2. Prolific, white flowers.

BRIEF DESCRIPTION OF THE DRAWINGS

This new *Deutzia* sp. cultivar is illustrated by the accompanying photographs which show the plant's form, foliage, and flowers. The colors shown are as true as can be reasonably obtained by conventional photographic procedures. Colors in the photographs may differ slightly from the color values cited in the detailed botanical description, which accurately describe the colors of the new cultivar.

DETAILED BOTANICAL DESCRIPTION

Figure 1:
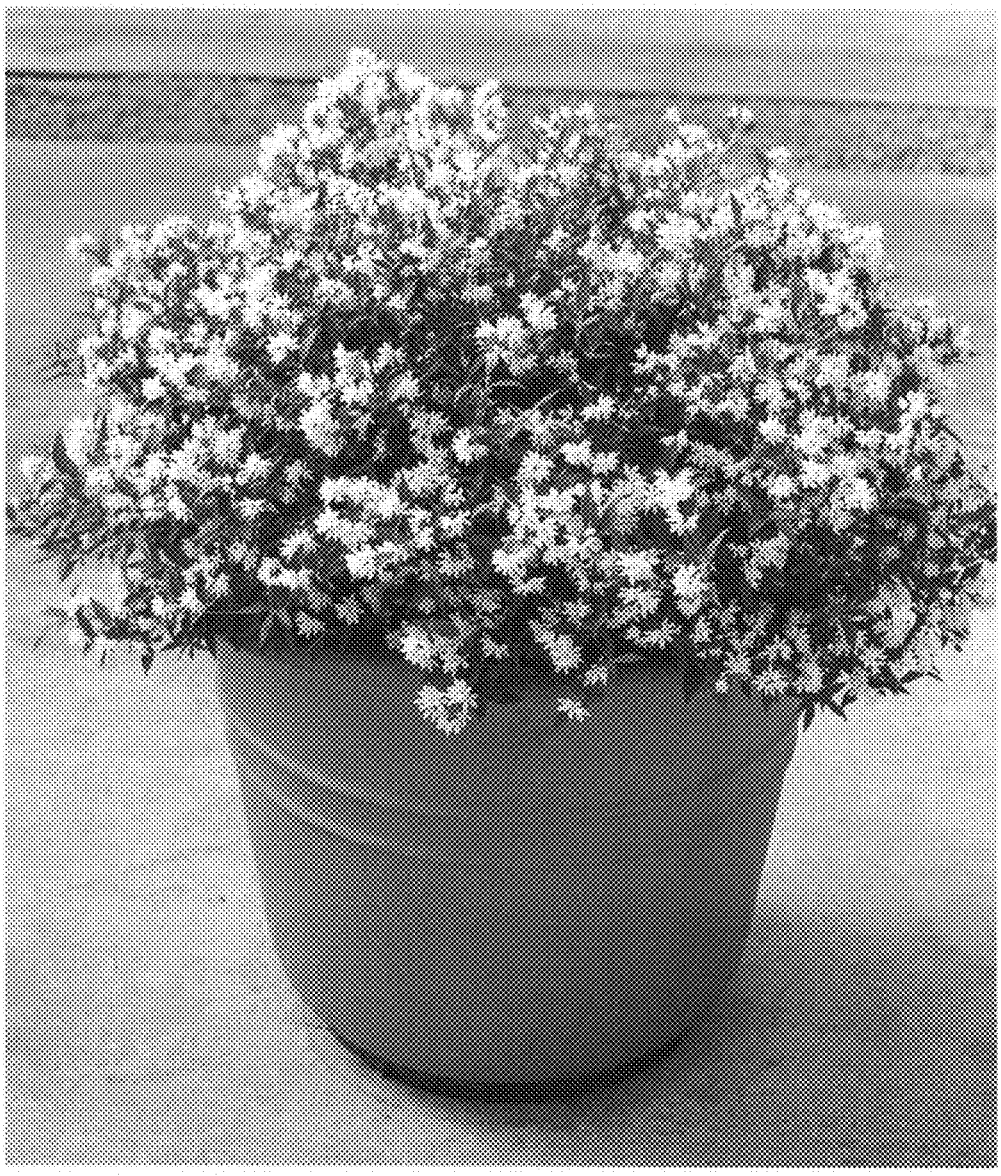
FIG. 1 is a color photograph of and individual plant of 'NCDX1', age three years, in bloom taken in Grand Haven, Mich.
Figure 2:
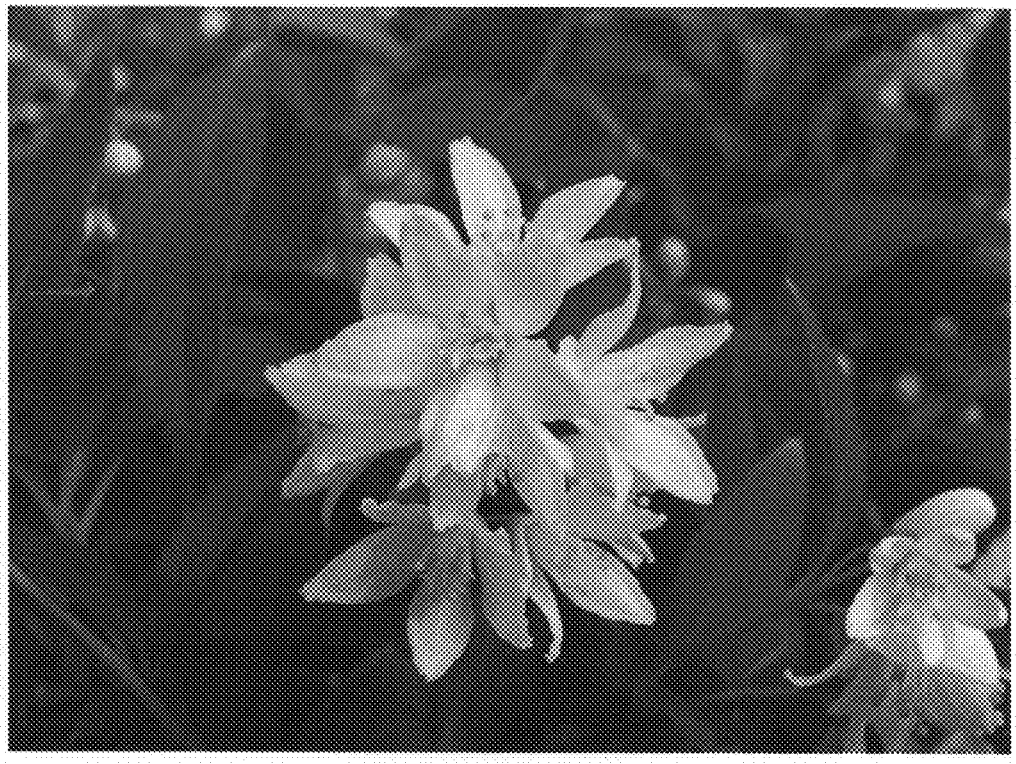
FIG. 2 is a color photograph of the panicled inflorescence of 'NCDX1', age three years, taken in Mills River, N.C."

The following is a detailed description of the botanical characteristics of the new and distinct variety of *Deutzia* sp. plant known by the denomination 'NCDX1'. The detailed description was taken on three-year-old plants growing in containers in a greenhouse in Mills River, N.C. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety.

Classification:

*Botanical name.*—*Deutzia* 'NCDX1'.

*Common name.*—*Deutzia.*

*Denomination.*—'NCDX1'.

Parentage:

*Female parent.*—*Deutzia gracilis* 'Nikko' (not patented).

*Male parent.*—*Deutzia×rosea* (*gracilis×purpurascens*) 'Carminea' (not patented).

Plant description:

*General appearance.*—Deciduous shrub. Compact, rounded/spreading form.

*Plant height.*—About 25 cm. after 2 years.

*Plant diameter or spread.*—About 800 cm. after 2 years.

*Primary lateral branches.*—Internode Length: About 29 mm. Texture: Smooth, glabrous, both upper and lower surfaces. Color: 141 C, both upper and lower surfaces.

*Foliage description.*—Type: Simple. Arrangement: Opposite. Length: About 5 cm. Width: About 1.5 cm. Shape: Lanceolate. Apex: Accuminate. Base: Attenuate. Margin: Slightly serrate. Texture: Upper surfaces scabrous; lower surface glabrous. Venation pattern: Pinnate. Color: Developing and fully expanded foliage: upper surface close to 137B; venation, same as lamina. Developing and fully expanded foliage: lower surface close to 137B; venation, same as lamina. Petiole: Length: About 8 mm. Diameter: About 3 mm. Texture, upper and lower surfaces glabrous. Color, upper and lower surfaces: 144B.

*Flower description.*—Flower type and habit: Single, star shaped flowers arranged on terminal panicles. Very freely flowering with about 9-18 flowers per inflorescence and about 100 flowers on each lateral branch. Flowers last about three to four weeks on the plant. Fragrance: Flowers slightly fragrant, sweet. Flower diameter: About 12-18 mm. Flower depth: About 10 mm. Flower buds: Length: About 7.6 mm. Diameter: About 3 mm. Shape: Ovoid. Color: 155 B. Petals: Quantity: Five per flower. Length About 7 mm. Shape: Elliptic. Apex: Obtuse to acute. Base: Attenuate. Margin: Entire. Texture: Upper and lower surfaces, Smooth, glabrous. Color: When opening, upper and lower surfaces: 155 D. Fully opened, upper and lower surfaces: 155 D. Sepals: Quantity: About six. Calyx length: About 3.8 mm. Calyx diameter: About 3.5 mm. Shape: Lanceolate. Apex: Acute. Margin: Entire. Texture: upper and lower surfaces: smooth, glabrous. Color: upper and lower surfaces: 145 B. Peduncles: Length: About 28 mm. Diameter: About 1 mm. Texture: Smooth, glabrous. Color: 143C. Pedicels: Length: About 4.2 mm. Diameter: About 0.5 mm. Texture: Smooth, glabrous. Color: 143C.

*Flowering season.*—Outdoors, flowering is continuous during the month of May in Mills River, N.C.

*Reproductive organs.*—Stamens: Quantity: Ten per flower. Anther shape: Round. Anther length: Less than 1 mm. Anther color: 12C. Pollen amount: Scarce. Pollen color: 12C. Pistils: Quantity: Five per flower. Pistil length: About 5 mm. Stigma color: 155D. Style length: About 5 mm. Style color: 155D. Ovary color: 146A.

*Seeds/fruit.*—Seed and fruit development has not been observed to date.

Disease/pest resistance: 'NCDX1' has not been observed to be susceptible to any particular diseases or insects.

Comparison with Known Varieties

While *Deutzia* 'Duncan' (U.S. Plant Pat. No. 16,098) has yellow green (151D) foliage, *Deutzia* sp. 'NCDX1' has dark green (137B) foliage. While *Deutzia* 'Kolmaspri' (U.S. Plant Pat. No. 20,964) has an upright habit and reaches 100 cm in height, *Deutzia* sp. 'NCDX1' has a rounded spreading form and reaches only 25 cm in height after two years.

What is claimed is:

1. A new and distinct variety of *Deutzia* plant named 'NCDX1,' substantially as illustrated and described herein.

* * * * *